United States Patent
Ishida et al.

(10) Patent No.: US 11,348,272 B2
(45) Date of Patent: May 31, 2022

(54) VEGETATION INDEX CALCULATION APPARATUS, VEGETATION INDEX CALCULATION METHOD, AND COMPUTER READABLE RECORDING MEDIUM

(71) Applicant: NEC Corporation, Tokyo (JP)

(72) Inventors: Kousuke Ishida, Tokyo (JP); Hajime Ishikawa, Tokyo (JP); Shinji Oominato, Tokyo (JP); Shunsuke Akimoto, Tokyo (JP); Masami Sakaguchi, Tokyo (JP); Shintaro Matsumoto, Tokyo (JP)

(73) Assignee: NEC CORPORATION, Tokyo (JP)

( * ) Notice: Subject to any disclaimer, the term of this patent is extended or adjusted under 35 U.S.C. 154(b) by 60 days.

(21) Appl. No.: 16/496,229

(22) PCT Filed: Feb. 22, 2018

(86) PCT No.: PCT/JP2018/006583
§ 371 (c)(1),
(2) Date: Sep. 20, 2019

(87) PCT Pub. No.: WO2018/173622
PCT Pub. Date: Sep. 27, 2018

(65) Prior Publication Data
US 2020/0058132 A1 Feb. 20, 2020

(30) Foreign Application Priority Data
Mar. 23, 2017 (JP) .............................. JP2017-057782

(51) Int. Cl.
| | | |
|---|---|---|
| *G06T 7/60* | (2017.01) | |
| *G06K 9/00* | (2022.01) | |
| *G06V 20/10* | (2022.01) | |

(52) U.S. Cl.
CPC ............. *G06T 7/60* (2013.01); *G06V 20/188* (2022.01); *G06T 2207/10012* (2013.01); *G06T 2207/10032* (2013.01); *G06T 2207/30188* (2013.01)

(58) Field of Classification Search
CPC ............ G01N 33/0098; G06K 9/00657; G06T 2207/10012; G06T 2207/10032; G06T 2207/30188; G06T 7/60
See application file for complete search history.

(56) References Cited

U.S. PATENT DOCUMENTS 10,438,343 B2 * 10/2019 Baurer ................ G06F 16/5866
10,796,150 B2 * 10/2020 Ganssle ................ A01G 22/00
(Continued)

FOREIGN PATENT DOCUMENTS

| JP | 2004-12233 A | 1/2004 |
|---|---|---|
| JP | 2006-252529 A | 9/2006 |

(Continued)

OTHER PUBLICATIONS

Extended European Search Report issued in European Patent Application No. 18771275.7, dated Mar. 20, 2020, 7 pages.
(Continued)

*Primary Examiner* — Bobbak Safaipour

(57) ABSTRACT

A vegetation index calculation apparatus (10) is provided with a specification unit (11) that collates height distribution data indicating a distribution of the height of plants that exist in a target region with predicted height data of a crop targeted for calculation of a vegetation index, and specifies a region where the crop exists within the target region, and a vegetation index calculation unit (12) that calculates the vegetation index of the crop that exists in the region specified by the specification unit (11).

6 Claims, 5 Drawing Sheets

(56) References Cited

U.S. PATENT DOCUMENTS

| | | | |
|---|---|---|---|
| 10,891,482 B2* | 1/2021 | Gurzoni, Jr. | G06V 10/993 |
| 11,076,589 B1* | 8/2021 | Sibley | G06V 20/188 |
| 2004/0264762 A1 | 12/2004 | Mas et al. | |
| 2007/0280528 A1 | 12/2007 | Wellington et al. | |
| 2010/0021052 A1 | 1/2010 | Wellington et al. | |
| 2010/0286973 A1* | 11/2010 | Messina | A01H 1/04 703/11 |
| 2013/0198693 A1* | 8/2013 | Jost | G06T 13/60 715/848 |
| 2014/0025305 A1 | 1/2014 | Rojas | |
| 2016/0063420 A1 | 3/2016 | Tomii et al. | |
| 2016/0309659 A1* | 10/2016 | Guy | A01G 25/16 |
| 2018/0039600 A1* | 2/2018 | Noland | B64C 39/024 |
| 2018/0350054 A1* | 12/2018 | Fox | A01G 7/06 |
| 2019/0057460 A1* | 2/2019 | Sakaguchi | A01D 75/00 |
| 2020/0166496 A1* | 5/2020 | Fujiyama | G01N 21/359 |
| 2020/0250597 A1* | 8/2020 | Fujiyama | A01G 7/00 |
| 2021/0027397 A1* | 1/2021 | Kikuchi | G06Q 50/02 |
| 2021/0142056 A1* | 5/2021 | Ishida | G06K 9/6272 |

FOREIGN PATENT DOCUMENTS

| | | |
|---|---|---|
| JP | 2011-223915 A | 11/2011 |
| JP | 2012-243226 A | 12/2012 |
| JP | 2015-188333 A | 11/2015 |
| JP | 2016-049102 A | 4/2016 |
| WO | WO-2012/134961 A2 | 10/2012 |

OTHER PUBLICATIONS

International Search Report corresponding to PCT/JP2018/006583, 2 pages, dated May 15, 2018.

Jensen, et al., Discrete return lidar-based prediction of leaf area index in two conifer forests, Remote Sending of Environment, 2008, vol. 112, p. 3947-3957.

* cited by examiner

VEGETATION INDEX CALCULATION APPARATUS, VEGETATION INDEX CALCULATION METHOD, AND COMPUTER READABLE RECORDING MEDIUM

CROSS-REFERENCE TO RELATED APPLICATIONS

This application is a national stage application of International Application No. PCT/JP2018/006583 entitled "VEGETATION INDEX CALCULATION APPARATUS, VEGETATION INDEX CALCULATION METHOD, AND COMPUTER READABLE RECORDING MEDIUM," filed on Feb. 22, 2018, which claims the benefit of the priority of Japanese Patent Application No. 2017-057782 filed on Mar. 23, 2017, the disclosures of each of which are hereby incorporated by reference in their entirety.

TECHNICAL FIELD

The present invention relates to a vegetation index calculation apparatus and a vegetation index calculation method that are for calculating a vegetation index of plants, and, furthermore, to a computer readable recording medium for realizing the apparatus and method.

BACKGROUND ART

In recent years, efforts have been made to predict crop yields by computer simulation following advances in computers. For example, Patent Document 1 proposes a system that predicts crop yields by ascertaining the growth condition of crops in a field.

Specifically, the system disclosed in Patent Document 1, first, calculates a vegetation index of the crop and an effective cumulative temperature, for every period, for a specific field (or area), based on satellite data and meteorological data, and generates a growth curve of the crop up to the present time using the calculated data. Next, the system disclosed in Patent Document 1 generates a statistical model using the obtained growth curve, and predicts a future growth curve using the generated statistical model.

Also, in such a system, the accuracy of the vegetation index of the crop is important. An example of a known vegetation index is NDVI (Normalized Difference Vegetation Index). NDVI is an index that utilizes the characteristics of plant leaves absorbing blue and red wavelengths and strongly reflecting wavelengths in the near-infrared region, and indicates the distribution and activity of vegetation. The tendency is for vegetation to be thicker as the value of NDVI becomes a larger positive value.

LIST OF RELATED ART DOCUMENTS

Patent Document

Patent Document 1: Japanese Patent Laid-Open Publication No. 2015-188333

SUMMARY OF INVENTION

Problems to be Solved by the Invention

Incidentally, NDVI is calculated by normalizing a value obtained by (IR−R)/(IR+R) between −1 and +1, where R is the reflectance of the red visible region obtained from satellite data, and IR is the reflectance of the near-infrared region obtained from satellite data. In other words, NDVI is calculated from data obtained by satellite.

However, since plants other than the crop, such as weeds, for example, also proliferate in an actual field, NVDI is a value that includes weed vegetation, Thus, the reliability of NDVI may be low, and in such cases, the predictive accuracy of crop yields drops markedly.

An example object of the invention is to provide a vegetation index calculation apparatus, a vegetation index calculation method and a computer readable recording medium that solve the above problems and can accurately calculate a vegetation index of a targeted crop in a specific field or area.

Means for Solving the Problems

A vegetation index calculation apparatus according to an example aspect of the invention includes:

a specification unit configured to collate height distribution data indicating a distribution of a height of plants that exist in a target region with predicted height data of a crop targeted for calculation of a vegetation index, and specify a region where the crop exists within the target region; and a vegetation index calculation unit configured to calculate the vegetation index of the crop that exists in the region specified by the specification unit.

A vegetation index calculation method according to an example aspect of the invention includes:

(a) a step of collating height distribution data indicating a distribution of a height of plants that exist in a target region with predicted height data of a crop targeted for calculation of a vegetation index, and specifying a region where the crop exists within the target region; and (b) a step of calculating the vegetation index of the crop that exists in the region specified in the (a) step.

Furthermore, a computer readable recording medium according to an example aspect of the invention includes a program recorded thereon, the program including instructions that cause a computer to carry out:

(a) a step of collating height distribution data indicating a distribution of a height of plants that exist in a target region with predicted height data of a crop targeted for calculation of a vegetation index, and specifying a region where the crop exists within the target region; and (b) a step of calculating the vegetation index of the crop that exists in the region specified in the (a) step.

Advantageous Effects of the Invention

As described above, according to the invention, a vegetation index of a targeted crop can be accurately calculated in a specific field or area.

EXAMPLE EMBODIMENTS

Example Embodiment

Hereinafter, a vegetation index calculation apparatus, a vegetation index calculation method and a program in an example embodiment of the invention will be described, with reference to FIGS. 1 to 5.

(Apparatus Configuration)

Figure 1:
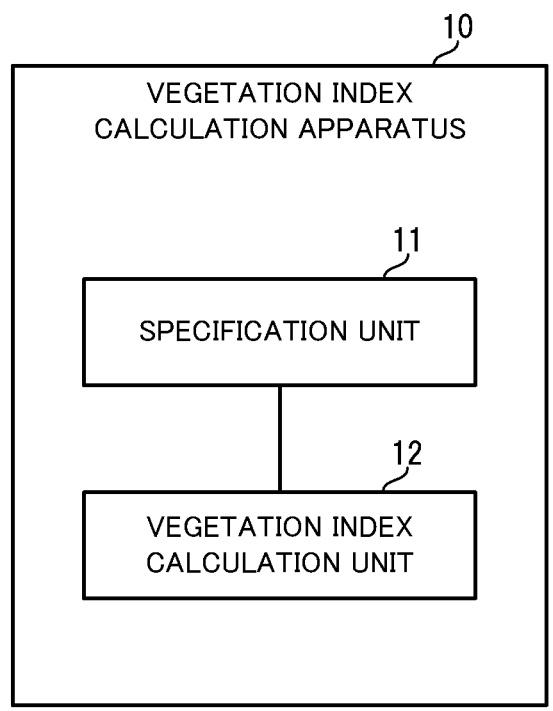
FIG. 1 is a block diagram showing a schematic configuration of a vegetation index calculation apparatus in an example embodiment of the invention.

Initially, a schematic configuration of the vegetation index calculation apparatus in the example embodiment will be described, using FIG. 1. FIG. 1 is a block diagram showing the schematic configuration of the vegetation index calculation apparatus in the example embodiment of the invention.

A vegetation index calculation apparatus 10 shown in FIG. 1 is an apparatus for calculating a vegetation index of a target region, such as a specific field or area, for example. As shown in FIG. 1, the vegetation index calculation apparatus 10 is provided with a specification unit 11 and a vegetation index calculation unit 12.

The specification unit 11, first, acquires height distribution data. The height distribution data is data indicating the distribution of the height of plants that exists in the target region. The height distribution data is data that indicates the distribution of the height of plants in the target region, in a manner such as a region R1 in which the plant height is less than M (unit is omitted), a region R2 in which the plant height is greater than or equal to M and less than N, and a region R3 in which the plant height is greater than or equal to N in the target region, for example. The way of deciding the heights when dividing the regions and the number of regions are not particularly limited. Also, for example, the heights of the plants within each region can be averaged, and the average height can be taken as the height of the plants in the respective regions. Specifically, a value obtained by averaging envelope curves indicating the heights of the plants can be used as the average height.

Next, the specification unit 11 collates the height distribution data with predicted height data of the crop targeted for calculation of a vegetation index, and specifies a region where the crop exists within the target region.

The vegetation index calculation unit 12 calculates a vegetation index of the crop that exists in the region specified by the specification unit 11.

In this way, in the example embodiment, the specification unit 11 compares height distribution data relating to the actual height distribution of plants in a target region with height data predicted in relation to the height of the crop targeted for calculation of a vegetation index. Therefore, the specification unit 11 is able to specify a region where a crop targeted for calculation of a vegetation index exists in the target region, even when there are plants other than the crop. Thus, according to the example embodiment, a vegetation index of a targeted crop can be accurately calculated in a specific field or area.

Figure 2:
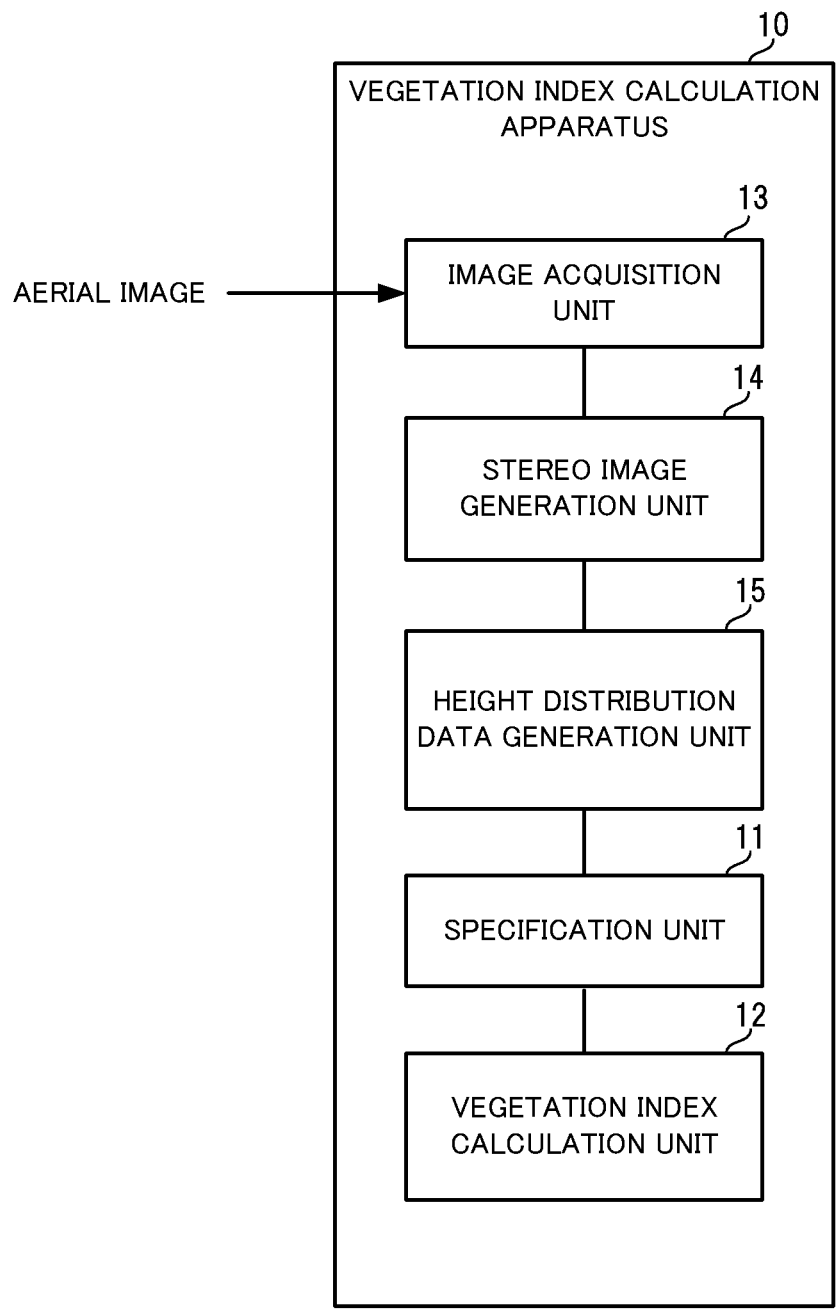
FIG. 2 is a block diagram showing a specific configuration of the vegetation index calculation apparatus in the example embodiment of the invention.
Figure 3:
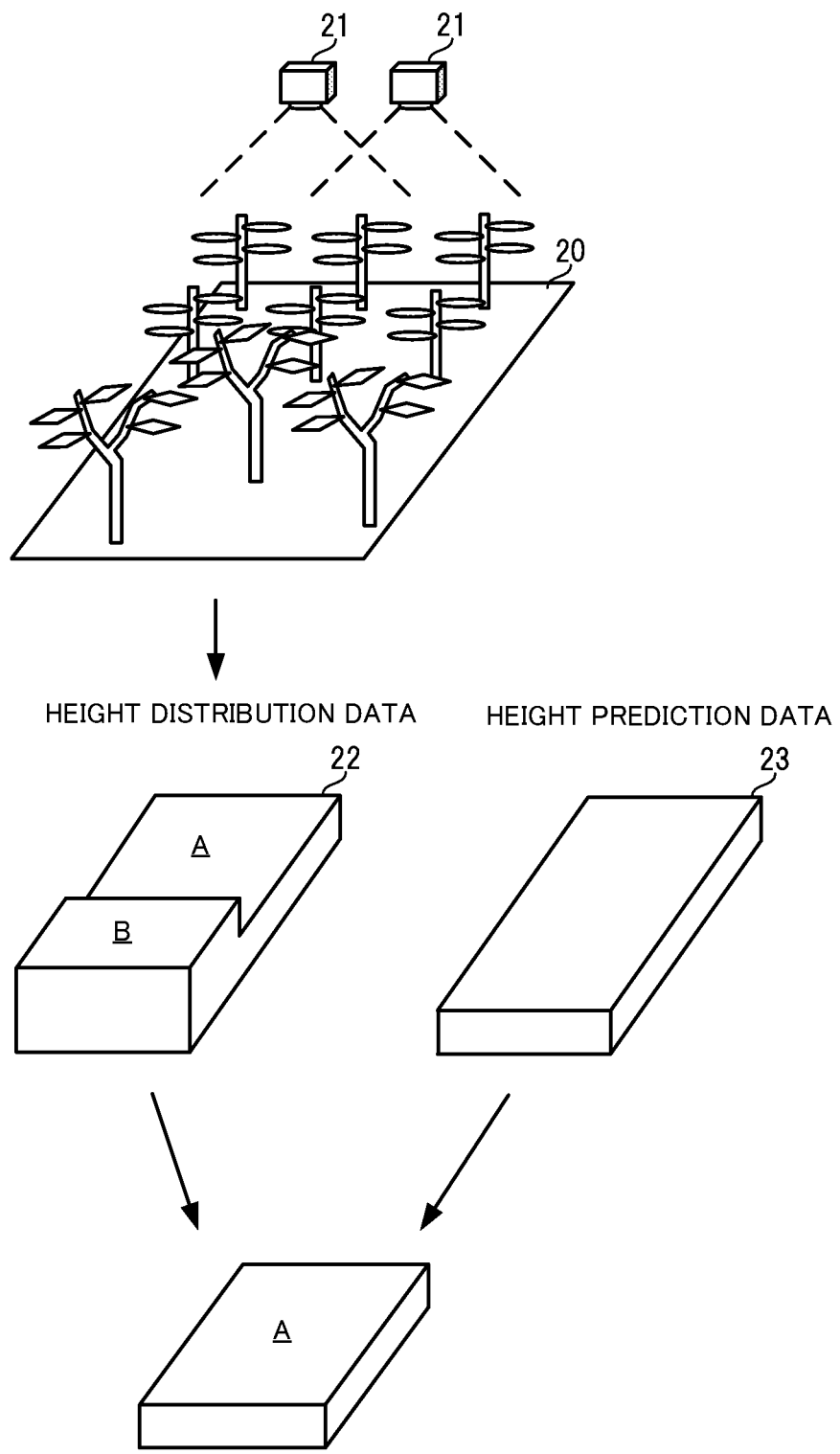
FIG. 3 is an illustrative diagram illustrating processing that is performed by the vegetation index calculation apparatus in the example embodiment of the invention.

Next, a specific configuration of the vegetation index calculation apparatus 10 in the example embodiment will be described, using FIGS. 2 and 3. FIG. 2 is a block diagram showing a specific configuration of the vegetation index calculation apparatus in the example embodiment of the invention. FIG. 3 is a diagram illustrating processing performed by the vegetation index calculation apparatus in the example embodiment of the invention.

As shown in FIG. 2, in the example embodiment, the vegetation index calculation apparatus 10 is provided with an image acquisition unit 13, a stereo image generation unit 14 and a height distribution data generation unit 15, in addition to the specification unit 11 and vegetation index calculation unit 12 described above.

The image acquisition unit 13 acquires an aerial image of the target region. The image acquisition unit 13 acquires an aerial image of a field or the like taken from the sky by a satellite, a plane, a drone or the like, for example.

The stereo image generation unit 14 generates a stereo image of the target region from the aerial image acquired by the image acquisition unit 13. The stereo image is an image generated from images obtained by shooting a target region 20 from the sky from different viewpoints, as shown in FIG. 3. The taking of images for generating a stereo image is usually performed by two cameras 21 mounted in parallel in a satellite, a plane, a drone or the like. The taking of images for generating a stereo image may be performed by one camera 21 while changing the shooting position. Note that generation of a stereo image includes selecting a pair of images to serve as the stereo image from aerial images acquired by the image acquisition unit 13.

The height distribution data generation unit 15 calculates the heights of plants that exist in the target region 20, by performing stereo matching processing on the stereo image generated by the stereo image generation unit 14. Also, the height distribution data generation unit 15, upon calculating the heights of the plants that exist in the target region 20, generates height distribution data 22 of the plants in the target region 20, as shown in FIG. 3, using the calculated heights.

Specifically, the height distribution data generation unit 15 divides each of the images constituting the stereo image into image blocks of certain size, for example. Next, the height distribution data generation unit 15 selects an arbitrary image block from one of the images constituting the stereo image, compares this selected image block with each image block of the other image constituting the stereo image, and specifies an image block of the other image that matches the selected image block.

Also, the height distribution data generation unit 15 performs similar processing for all the image blocks of the one image, and specifies the corresponding image block in the other image for each of the image blocks of the one image. Pairs of image blocks of the one image and image blocks of the other image that match each other are thereby created.

Next, the height distribution data generation unit 15 specifies, for each pair of matching image blocks, a point at which the image blocks correspond to each other as a corresponding point. Next, the height distribution data generation unit 15 superimposes the one image and the other image, and calculates the disparity between the specified corresponding points for every pair of matching image blocks. Thereafter, the height distribution data generation unit 15 calculates, for every pair of matching image blocks, the height of the corresponding point by executing triangulation, using the calculated disparity and the distance from the image capturing apparatus that took the aerial image to the target region. The height of a corresponding point that corresponds to a plant is the height of the plant.

The specification unit 11, in the example embodiment, acquires data (height prediction data) 23 predicted in relation to the height of the crop targeted for calculation of a vegetation index, as shown in FIG. 3. The height prediction data 23 may be calculated using any technique.

For example, first, a virtual field is generated on a computer, based on field information including at least one of weather information, soil information, crop information, crop growth information and agricultural management history information of a field. Next, in this virtual field, growth simulation that uses a crop growth model is executed in this virtual field, and the height of the crop under a predetermined condition (e.g., predetermined time) is predicted from the execution result. Note that the height in this case may be height of the crop from the ground to the highest point reached, or may be the predicted height indicated by the envelope curve of the crop.

Next, the specification unit 11 collates the height prediction data 23 with the height distribution data 22 generated by the height distribution data generation unit 15, and specifies a region where the crop exists within the target region 20.

In the example in FIG. 3, the height distribution data 22 indicates a region A and a region B where the plants have different heights. The height of the crop shown by the height prediction data 23 coincides with the height of the region A. Thus, the specification unit 11 specifies the region A as a region where the crop targeted for calculation of a vegetation index exists. Note that the height distribution data 22 and the height prediction data 23 are actually numeric data, but are shown conceptually in FIG. 3.

Also, apart from specifying a region where the height distribution data 22 matches the height prediction data 23 as a region where the crop exists, it is also possible; if the crop and plants other than the crop can be distinguished, to specify a region where the height distribution data 22 matches the height prediction data 23 with a width of a predetermined numerical value as a region where the crop exists.

The vegetation index calculation unit 12 calculates a vegetation index of the crop that is being grown in the region specified by the specification unit 11. Specifically, the vegetation index calculation unit 12 receives notification of a region where the crop exists from the specification unit 11, and specifies an image of the region where the crop exists within the aerial image of the target region 20. The vegetation index calculation unit 12 then calculates a vegetation index of the crop from the specified image. Note that the specification unit 11 may specify the image of the region where the crop exists within the serial image of the target region 20.

SAVI (Soil Adjusted Vegetation Index), WDVI (Weighted Difference Vegetation Index, and NDRE (Normalized Difference Red Edge) are given as examples of the vegetation index that is calculated in the example embodiment, in addition to NDVI mentioned in the Background Art.

SAVI is an index obtained by taking the effects of reflection of the background soil into account in NDVI. WDVI is a weighted difference vegetation index, and is calculated by weighting each band of reflected light from a plant with the value of soil taken as 0. NDRE is an index obtained by normalizing values measured in a Red Edge band (near a wavelength of 710 nm) by RapidEye satellites.

(Apparatus Operations)

Figure 4:
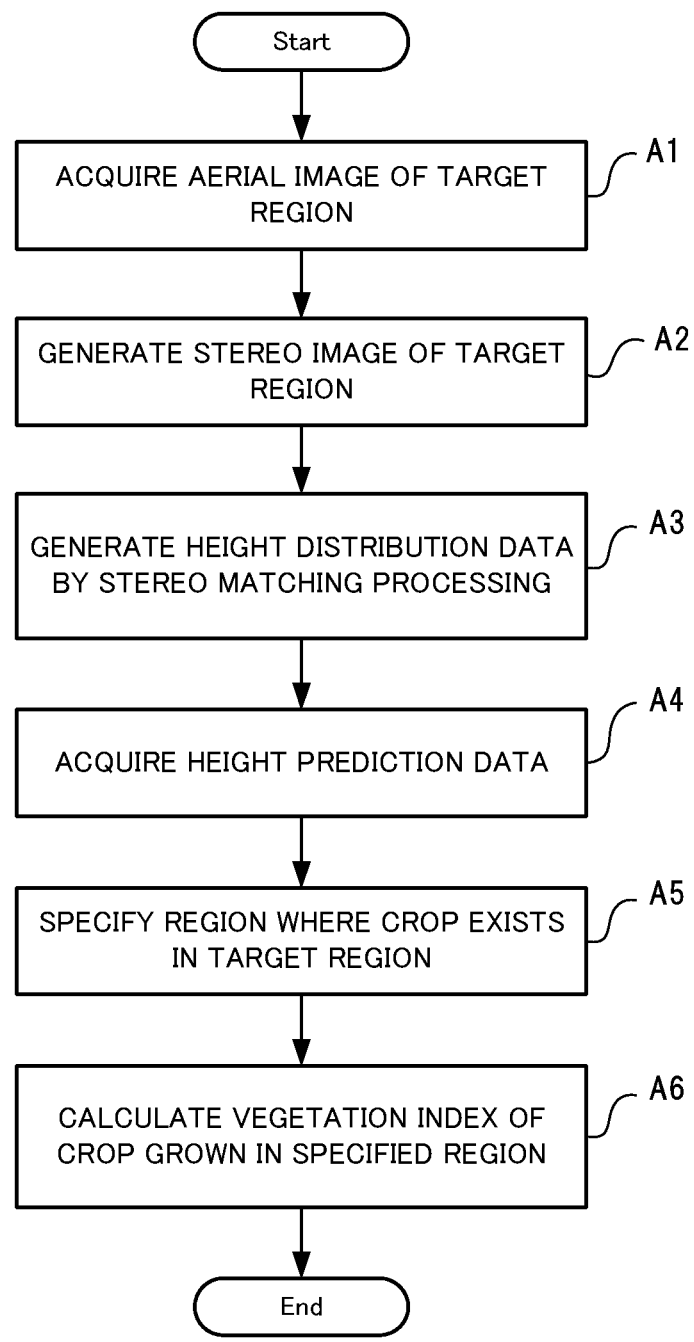
FIG. 4 is a flowchart showing operations of the vegetation index calculation apparatus in the example embodiment of the invention.

Next, operations of the vegetation index calculation apparatus 10 in the example embodiment will be described using FIG. 4. FIG. 4 is a flowchart showing operations of the vegetation index calculation apparatus 10 in the example embodiment of the invention. In the following description, FIGS. 1 to 3 will be referred to as appropriate. Also, in the example embodiment, a vegetation index calculation method is implemented by operating the vegetation index calculation apparatus 10. Therefore, description of the vegetation index calculation method in the example embodiment will be replaced by the following description of the operations of the vegetation index calculation apparatus 10.

As shown in FIG. 4, initially, the image acquisition unit 13 acquires an aerial image of the target region 20 (step A1). Next, the stereo image generation unit 14 generates a stereo image of the target region 20 (step A2). The stereo image generation unit 14 passes the generated stereo image to the height distribution data generation unit 15.

Next, the height distribution data generation unit 15 calculates the heights of plants that exist in the target region 20, by performing stereo matching processing on the stereo image generated by the stereo image generation unit 14, and generates height distribution data 22 of the plants in the target region 20, using the calculated heights (step A3). The height distribution data generation unit 15 passes the generated height distribution data 22 to the specification unit 11.

Next, the specification unit 11 acquires data (height prediction data) 23 predicted in relation to the height of the crop targeted for calculation of a vegetation index (step A4).

Next, the specification unit 11 collates the height prediction data 23 acquired in step A4 with the height distribution data 22 generated by the height distribution data generation unit 15 in step A3, and specifies a region where the crop exists in the target region 20 (step A5). The specification unit 11 notifies the specified region to the vegetation index calculation unit 12.

Next, the vegetation index calculation unit 12 calculates a vegetation index of the crop that is being grown in the region specified by the specification unit 11 in step A5 (step A6). Specifically, the vegetation index calculation unit 12 receives notification of the region where the crop exists from the specification unit 11, and specifies an image of the region specified in step A5 within the aerial image of the target region 20. The vegetation index calculation unit 12 then calculates a vegetation index (e.g., NDVI) of the crop from the specified image.

As described above, according to the example embodiment, a region where the crop exists is specified based on the height information on plants obtained from an aerial image. Thus, according to the example embodiment, a vegetation index of a targeted crop can be accurately calculated in a specific field or area.

Also, in steps A1 to A6 mentioned above, the height distribution data generation unit 15 generates the height distribution data 22 from a stereo image, but the example embodiment is not limited to this mode, and the height distribution data generation unit 15 may generate height distribution data by another technique.

Also, another apparatus (apparatus A) can be provided with the stereo image generation unit 14 and the height distribution data generation unit 15, instead of the vegetation index calculation apparatus 10. In this case, the aerial image acquired by the image acquisition unit 13 of the vegetation index calculation apparatus 10 is transmitted to the apparatus A, and generation of a stereo image and generation of height distribution data are performed in this apparatus A. The vegetation index calculation apparatus 10 then acquires the height distribution data from this apparatus A.

(Variation)

In the above description, a mode where the specification unit 11 compares height distribution data relating to the actual height distribution of plants in the target region with height data predicted in relation to the height of the crop targeted for calculation of a vegetation index is described.

Apart from this mode, the specification unit 11 is also able to compare height distribution data relating to the actual height distribution of the plants in a target region with height data predicted in relation to the height of plants other than the crop, such as weeds, for example, that can exist in the target region, and to specify a region where the weeds exist within the target region. In this case, the vegetation index calculation unit 12 is able to calculate a vegetation index of weeds that exist in a region specified by the specification unit 11, and correct the vegetation index calculated from the entire aerial image of the target region, using the vegetation index of the weeds. As a result of this correction, a vegetation index of the crop can be accurately calculated.

(Program)

The program in the example embodiment need only be a program that causes a computer to execute steps A1 to A6 shown in FIG. 4. The vegetation index calculation apparatus 10 and the vegetation index calculation method in the example embodiment can be realized, by this program being installed on a computer and executed. In this case, a processor of the computer functions and performs processing as the specification unit 11, the vegetation index calculation unit 12, the image acquisition unit 13, the stereo image generation Unit 14 and the height distribution data generation unit 15.

Also, the program in the example embodiment may be executed by a computer system built with a plurality of computers. In this case, for example, the computers may respectively function as one of the specification unit 11, the vegetation index calculation unit 12, the image acquisition unit 13, the stereo image generation unit 14 and the height distribution data generation unit 15.

Figure 5:
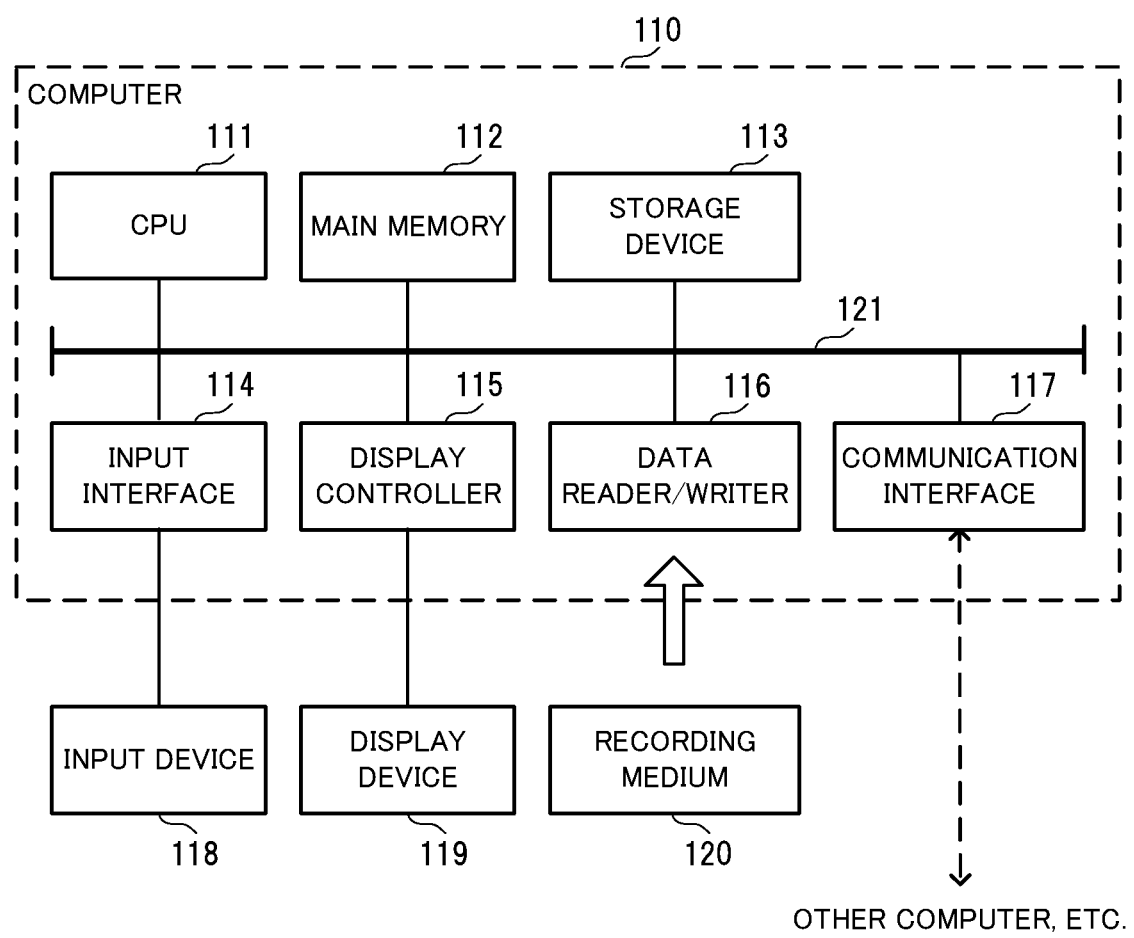
FIG. 5 is a block diagram showing an example of a computer that realizes the vegetation index calculation apparatus in the example embodiment of the invention.

Here, a computer that realizes the vegetation index calculation apparatus 10 by executing a program in the example embodiment will be described using FIG. 5. FIG. 5 is a block diagram showing an example of a computer that realizes the vegetation index calculation apparatus in the example embodiment of the invention.

As shown in FIG. 5, a computer 110 is provided with a CPU (Central Processing Unit) 111, a main memory 112, a storage device 113, an input interface 114, a display controller 115, a data reader/writer 116, and a communication interface 117. These units are connected to each other in a manner that enables data communication, via a bus 121. Note that the computer 110 may be provided with a GPU (Graphics Processing Unit) or a FPGA (Field-Programmable Gate Array) in addition to the CPU 111 or instead of the CPU 111.

The CPU 111 implements various computations, by extracting programs (code) of the example embodiment stored in the storage device 113 to the main memory 112, and executing these programs in a predetermined order. The main memory 112 is, typically, a volatile storage device such as a DRAM (Dynamic Random Access Memory). Also, the programs of the example embodiment can be provided in a state of being stored on a non-transitory computer readable recording medium 120. Note that the programs of the example embodiment may also be distributed on the Internet connected via the communication interface 117.

Also, a semiconductor memory device such as a flash memory is given as a specific example of the storage device 113, in addition to a hard disk drive. The input interface 114 mediates data transmission between the CPU 111 and an input device 118 such a keyboard and a mouse. The display controller 115 is connected to a display device 119, and controls display that is performed on the display device 119.

The data reader/writer 116 mediates data transmission between the CPU 111 and the recording medium 120, and executes reading out of programs from the recording medium 120, and writing of processing results of the computer 110 to the recording medium 120. The communication interface 117 mediates data transmission between the CPU 111 and other computers.

Also, a general-purpose semiconductor memory such as CF (Compact Flash (registered trademark)) and SD (Secure Digital), a magnetic recording medium such a flexible disk, or an optical recording medium such as CD-ROM (Compact Disk Read Only Memory) are given as specific examples of the recording medium 120.

Note that the vegetation index calculation apparatus 10 in the example embodiment is also realizable by using hardware that supports the various components, rather than a computer on which programs are installed. Furthermore, the vegetation index calculation apparatus 10 may be partly realized by programs, and the remaining portion may be realized by hardware.

The above example embodiment can also be partly or wholly represented by Supplementary Notes 1 to 9 described below, but is not limited to the following disclosure.

(Supplementary Note 1)

A vegetation index calculation apparatus including:

a specification unit configured to collate height distribution data indicating a distribution of a height of plants that exist in a target region with predicted height data of a crop targeted for calculation of a vegetation index, and specify a region where the crop exists within the target region; and a vegetation index calculation unit configured to calculate the vegetation index of the crop that exists in the region specified by the specification unit.

(Supplementary Note 2)

The vegetation index calculation apparatus according to Supplementary Note 1, further including:

an image acquisition unit configured to acquire an serial image of the target region;

a stereo image generation unit configured to generate a stereo image from the aerial image acquired by the image acquisition unit; and a height distribution data generation unit configured to calculate the heights of plants that exist in the target region, by performing stereo matching processing on the stereo image generated by the stereo image generation unit, and generate the height distribution data using the calculated heights, and in which the vegetation index calculation unit calculates the vegetation index of the crop, using an image of the region specified by the specification unit within the aerial image.

(Supplementary Note 3)

The vegetation index calculation apparatus according to Supplementary Note 1 or 2, in which the predicted height data of the crop is generated by performing growth simulation that uses a crop growth model, in a virtual field generated based on field information including at least one of weather information, soil information, crop information, crop growth information and agricultural management history information of a field.

(Supplementary Note 4)

A vegetation index calculation method including:

(a) a step of collating height distribution data indicating a distribution of a height of plants that exist in a target region with predicted height data of a crop targeted for calculation of a vegetation index, and specifying a region where the crop exists within the target region; and (b) a step of calculating the vegetation index of the crop that exists in the region specified in the (a) step.

(Supplementary Note 5)

The vegetation index calculation method according to Supplementary Note 4, further including:

(c) a step of acquiring an aerial image of e target region;

(d) a step of generating a stereo image from the aerial image acquired in the (c) step; and (e) a step of calculating the heights of the plants that exist in the target region, by performing stereo matching processing on the stereo image generated in the (d) step, and generating the height distribution data using the calculated heights, in which, in the (b) step, the vegetation index of the crop is calculated, using an image of the region specified in the (a) step within the aerial image.

(Supplementary Note 6)

The vegetation index calculation method according to Supplementary Note 4 or 5, in which the predicted height data of the crop is generated by performing growth simulation that uses a crop growth model, in a virtual field generated based on field information including at least one of weather information, soil information, crop information, crop growth information and agricultural management history information of a field.

(Supplementary Note 7)

A computer readable recording medium that includes a program recorded thereon, the program including instructions that cause a computer to carry out:

(a) a step of collating height distribution data indicating a distribution of a height of plants that exist in a target region with predicted height data of a crop targeted for calculation of a vegetation index, and specifying a region where the crop exists within the target region; and (b) a step of calculating the vegetation index of the crop that exists in the region specified in the (a) step.

(Supplementary Note 8)

The computer readable recording medium according to Supplementary Note 7, the program includes instructions that cause the computer to further carry out:

(c) a step of acquiring an aerial image of the target region;

(d) a step of generating a stereo image from the aerial image acquired in the (c) step; and (e) a step of calculating the heights of the plants that exist in the target region, by performing stereo matching processing on the stereo image generated in the (d) step, and generating the height distribution data using the calculated heights, in which, in the (b) step, the vegetation index of the crop is calculated, using an image of the region specified in the (a) step within the aerial image.

(Supplementary Note 9)

The computer readable recording medium according to Supplementary Note 7 or 8, in which the predicted height data of the crop is generated by performing growth simulation that uses a crop growth model, in a virtual field generated based on field information including at least one of weather information, soil information, crop information, crop growth information and agricultural management history information of a field.

Although the invention has been described above with reference to an example embodiment, the invention is not intended to be limited to the above example embodiment. A person skilled in the art will appreciate that the configurations and details of the invention can be variously modified within the scope of the invention.

This application is based upon and claims the benefit of priority from Japanese application No. 2017-57782 filed in Japan on Mar. 23, 2017, the disclosure of which is incorporated herein in its entirely.

INDUSTRIAL APPLICABILITY

As described above, according to the invention, a vegetation index of a targeted crop can be accurately calculated in a specific field or area. The invention is useful in a system that performs prediction of crop yields, which requires accurate vegetation index values.

LIST OF REFERENCE SIGNS

10 Vegetation index calculation apparatus
11 Specification unit
12 Vegetation index calculation unit
14 Stereo image generation unit
15 Height distribution data generation unit
20 Target region
21 Camera
22 Height distribution data
23 Height prediction data
110 Computer
111 CPU
112 Main memory
113 Storage device
114 Input interface
115 Display controller
116 Data reader/writer
117 Communication interface
118 Input device
119 Display device
120 Recording medium
121 Bus

The invention claimed is:

1. A vegetation index calculation apparatus comprising:
a specification unit that collates collate height distribution data indicating a distribution of a height of plants that exist in a target region with predicted height data of a crop targeted for calculation of a vegetation index, and specify a region where the crop exists within the target region; and
a vegetation index calculation unit that calculates the vegetation index of the crop that exists in the region specified by the specification unit,
wherein the predicted height data of the crop is generated by performing growth simulation that uses a crop growth model, in a virtual field generated based on field information including at least one of weather information, soil information, crop information, crop growth information and agricultural management history information of a field.

2. The vegetation index calculation apparatus according to claim 1, further comprising:
an image acquisition unit that acquires an aerial image of the target region;
a stereo image generation unit that generates a stereo image from the aerial image acquired by the image acquisition unit; and
a height distribution data generation unit that calculates the heights of plants that exist in the target region, by performing stereo matching processing on the stereo image generated by the stereo image generation unit, and generate the height distribution data using the calculated heights, wherein the vegetation index calculation unit calculates the vegetation index of the crop, using an image of the region specified by the specification unit within the aerial image.

3. A vegetation index calculation method comprising:
(a) collating height distribution data indicating a distribution of a height of plants that exist in a target region with predicted height data of a crop targeted for calculation of a vegetation index, and specifying a region where the crop exists within the target region; and
(b) calculating the vegetation index of the crop that exists in the region specified in the (a),
wherein the predicted height data of the crop is generated by performing growth simulation that uses a crop growth model, in a virtual field generated based on field information including at least one of weather information, soil information, crop information, crop growth information and agricultural management history information of a field.

4. The vegetation index calculation method according to claim 3, further comprising:
(c) acquiring an aerial image of the target region;
(d) generating a stereo image from the aerial image acquired in the (c); and
(e) calculating the heights of the plants that exist in the target region, by performing stereo matching processing on the stereo image generated in the (d), and generating the height distribution data using the calculated heights,
wherein, in the (b), the vegetation index of the crop is calculated, using an image of the region specified in the (a) within the aerial image.

5. A non-transitory computer readable medium that includes a program thereon, the program including instructions that cause a computer to carry out:
(a) a step of collating height distribution data indicating a distribution of a height of plants that exist in a target region with predicted height data of a crop targeted for calculation of a vegetation index, and specifying a region where the crop exists within the target region; and
(b) a step of calculating the vegetation index of the crop that exists in the region specified in the (a) step,
wherein the predicted height data of the crop is generated by performing growth simulation that uses a crop growth model, in a virtual field generated based on field information including at least one of weather information, soil information, crop information, crop growth information and agricultural management history information of a field.

6. The non-transitory computer readable medium according to claim 5,
wherein the program includes instructions that cause the computer to further carry out:
(c) a step of acquiring an aerial image of the target region;
(d) a step of generating a stereo image from the aerial image acquired in the (c) step; and
(e) a step of calculating the heights of the plants that exist in the target region, by performing stereo matching processing on the stereo image generated in the (d) step, and generating the height distribution data using the calculated heights,
wherein, in the (b) step, the vegetation index of the crop is calculated, using an image of the region specified in the (a) step within the aerial image.

* * * * *